United States Patent [19]

Evans et al.

[11] Patent Number: 5,310,662
[45] Date of Patent: May 10, 1994

[54] RECEPTORS: THEIR IDENTIFICATION, CHARACTERIZATION, PREPARATION AND USE

[75] Inventors: Ronald M. Evans, La Jolla; Stanley M. Hollenberg, Del Mar, both of Calif.

[73] Assignee: The Salk Institute for Biological Studies, La Jolla, Calif.

[21] Appl. No.: 73,928

[22] Filed: Jun. 8, 1993

Related U.S. Application Data

[62] Division of Ser. No. 278,614, Nov. 30, 1988, Pat. No. 5,217,867.

[51] Int. Cl.$^5$ .................... C12N 15/62; C12N 15/63
[52] U.S. Cl. .................... 435/64.1; 435/69.7; 435/252.3; 435/320.1; 436/501; 536/23.4
[58] Field of Search ............. 435/69.7, 252.3, 320.1; 436/501; 536/23.4; 430/69.1

[56] References Cited

U.S. PATENT DOCUMENTS 5,171,671 12/1992 Evans et al. .................... 435/69.1

OTHER PUBLICATIONS

Cell 46:645-652 (Aug. 29, 1986) Giguere et al. Functional Domains of the Human Glucocorticoid Receptor.
Science 240:889-895 (May 13, 1988) Evans The Steroid and Thyroid Hormone Receptor Superfamily.
Cell 49:39-46 (Apr. 10, 1987) Hollenberg et al. Colocalization of DNA-Binding and Transcriptional Activation Functions in the Human Glucocorticoid Receptor.

*Primary Examiner*—Robert J. Hill, Jr.
*Assistant Examiner*—John D. Ulm
*Attorney, Agent, or Firm*—Pretty, Schroeder, Brueggemann & Clark

[57] ABSTRACT

Disclosed are novel hormone and hormone-like receptors Wherein the trans-activation transcription domain(s) is modified in terms of position and/or copy number or otherwise versus parent receptor, such novel receptors having increased trans-activation transcription activation properties surprisingly superior to the parent receptor. Also disclosed are the recombinant methods and means for preparing such receptors and assays based upon the use of such receptors for screening and identifying putative materials that can affect such receptors and/or for the expression via induced transcription of a reporter or other desired, preferably heterologous gene or DNA product.

13 Claims, 4 Drawing Sheets

RECEPTORS: THEIR IDENTIFICATION, CHARACTERIZATION, PREPARATION AND USE

ACKNOWLEDGEMENT

This invention was made with Government supoprt under Grant No. 26444 awarded by the National Institutes of Health. The Government has certain rights in the invention.

This application is a divisional of application Ser. No. 07/278,614, filed Nov. 30, 1988 now U.S. Pat No. 5,217,867.

RELATED APPLICATIONS

Reference is made to U.S, patent application Ser. No. 922,585, filed Oct. 24, 1986 (now abandoned) and to its continuing application U.S. Ser. No. 108,471, filed Oct. 20, 1987, now issued as U.S. Pat. No. 5,071,773, counterparts of which exist as published documents by certain jurisdictions outside of the United States, and to U.S. Ser. No. 128,331, filed Dec. 2, 1987, (now abandoned) and to its continuing application U.S. Ser. No. 276,536, filed Nov. 30, 1988, now issued as U.S. Pat. No. 4,981,784. All of these applications refer in various respects to hormone receptors and compositions thereof, and to methods for their preparation, and use, particularly in novel assay systems. The entire disclosures of each of these applications is hereby incorporated by express reference herein.

FIELD OF THE INVENTION

The present invention relates generally to the identification and characterization of certain polypeptide sequences that function as transcription trans-activation domains, and to their preparation and use, particularly in the preparation of novel intracellular hormone or hormone-like receptors, for example, steroid receptor polypeptides, thyroid polypeptides and retinoid polypeptides including those of the human species, where advantage is provided in terms of transactivation transcription initiation activity by augmenting the effect of said domains.

More particularly, the present invention is directed to such novel receptor polypeptides, wherein the transcription trans-activation domains have been augmented in effect so as to produce novel entities that exhibit increased transcription initiation activity surprisingly superior to the parent molecule.

Novel aspects relating to the preparation of such transcription trans-activation molecules, including novel DNA isolates encoding same and the transcription trans-activation domains, expression vectors operatively harboring these DNA sequences and hosts transfected with said vectors are included within the scope of this invention.

Most particularly, the present invention concerns the use of the novel transcription transactivation hormone or hormone-like receptors of the present invention in assays for screening various putative materials that may have operative binding affinity for the novel hormone or hormone-like receptors hereof. In a preferred embodiment, this aspect of the invention provides an assay for screening such putative materials, for example, steroid agonists and antagonists in an enhanced, so-called trans-activation system.

BACKGROUND OF THE INVENTION

The patent applications cited supra disclose, inter alia., the characterization and preparation of various hormone and hormone-like receptors, including steroid, thyroid and retinoid receptors such as those represented by the glucocorticoid, mineralcorticoid, thyroid, estrogen related and retinoid classes, and specifically, the glucocorticoid, estrogen, aldosterone and retinoic acid receptors themselves. These specific receptors have been the subject of considerable research and form the particular bases for the inventions disclosed and claimed in these patent applications. Similarly, the extant, parallel scientific literature has focused on the specific receptors listed above from among the classes of receptors that exist.

It is known, for example, that the glucocorticoid receptor belongs to a large super-family of ligand-dependent transcription factors that have themselves diverse roles in homeostasis, growth and development. Comparison of complementary DNAs encoding these receptors, as well as mutational analyses of their coding sequences have identified certain functional domains within the molecule that are thought responsible respectively for DNA binding, hormone binding and nuclear localization. See Evans, et al., *Science* 240, 889 (1988) for a review of this subject matter. In the case of the glucocorticoid receptor, the so-called DNA binding domain spans some sixty-six amino acids and is highly conserved among various species and this domain has been found to be required in order to activate transcription. See Hollenberg, et al., *Cell* 49, 39 (1987), Miesfeld, et al., *Science* 236, 423 (1987), Danielsen, et al., *Mol.Endo* 1, 816 (1987), Kumar, et al., *Cell* 51, 941 (1987), Gronemeyer, *EMBO J.* 6, 3985 (1987), and Waterman, et al., *Mol,Endo* 2, 14 (1988). This region has been found to contain nine invariant cysteines residues and although the contribution of each cysteine residue to overall function is unknown, as is the actual structure formed by this domain, it has been proposed that these cysteine residues coordinate two zinc ions to form two DNA binding, so-called finger domains which result in a ternary structure thought responsible for its localization and binding to the requisite DNA site. See Klug, et al.. *Tr.Biochem.Sci* 12, 464 (1987), Bens, et al., *Cell* 52, 1 (1988), and Evans, supra.

In a location nearer the carboxy-terminal end distal from the DNA binding region is the so-called ligand binding domain which has the demonstrated ability to block activity of the receptor in the absence of hormone. Thus, presence of the requisite hormone relieves the inhibition of the receptor to activity. Deletion of this region has been found to produce a hormone-independent transcription activator. See Godowski, et al., *Nature* 325. 365 (1987), Hollenberg, et al., supra, Kumar, et al., supra. Danielsen et al., supra, and Adler et al., *Cell* 52, 685 (1988).

In contrast to these two domains, the sequences lying towards the amino-terminal region from the DNA binding domain are poorly understood both as to structure, and particularly, function. This region is extremely variable both in size and in composition amongst the various receptors—See Evans, supra—and may contribute to the heterogeneity of receptor function. See Kumar et al., supra, and Tora et al., 333, 185 (1988).

Despite extensive analysis, some of which having been reported in the scientific literature, the region(s) that determines trans-activation of transcription initiation remains poorly characterized. Trans-activation domains can be defined as polypeptide regions that, when combined with the DNA binding functional domain, increase productive transcription initiation by RNA polymerases. See Sigler, *Nature* 333, 210 (1988), Brent et al., *Cell* 43. 729 (1985), Hope et al., *Cell* 46, 885 (1986), Ma et al., *Cell* 48, 847 (1987), Ma et al., *Cell* 51, 113 (1987), Lech et al., *Cell* 52, 179 (1988), and Hope et al., *Nature* 333, 635 (1988).

Previous research of the human glucocorticoid receptor by linker scanning mutagenesis identified two regions outside of the DNA binding region having a role in transcription activation. These regions were defined as $\tau_1$ and $\tau_2$. Giguere et al., *Cell* 46, 645 (1986). Further research from these laboratories has also resulted in the report of a co-localization of transactivation and DNA binding functions. See Hollenberg et al., supra. Miesfeld, et al., supra. Danielsen et al., supra, and Waterman et al., supra. As a composite, this research has given rise merely to an emerging picture of an increasingly modular molecule with discrete domains, each contributing to the identified properties of ligand-binding, DNA-binding and trans-activation of transcription. However, until now, the region(s) determining the trans-activation activity, was not at all well understood. Thus, the picture based upon existing research lacks an appreciation of the dynamic nature of the steroid receptors and how the various domains determine the cascade of events initiated by ligand-binding and consummated by promoter-specific transactivation.

Further, although previous research has identified functional "domains", there has been little systematic effort to identify amino acids that contribute to the specific activities of the molecule itself. Thus, the previous identification of steroid receptor transactivation regions resulted only from a demonstrated loss of activity via deletion or insertional mutagenesis, but in no case have the properties of the regions themselves been confirmed in assays that reflect a dominant gain of function.

Thus, Godowski et al., *Science* 241, 812 (1988), report results that show that the glucocorticoid receptor contains at least one "enhancement domain" other than that overlapping the glucocorticoid response element binding region and that the second domain occupies a region near the receptor amino-terminus. Similarly, Webster et al., *Cell* 54, 199 (1988) report on an inducible transcription activation function of the estrogen and glucocorticoid receptors, and these researchers speculate that the relative positions of the hormone regions (i.e., ligand and DNA-binding domains) are not important for the transcription induction activity of the receptor. Yet, these researchers admit that they have no definition of the exact location and nature of what they call the hormone-inducible activating domain, to say nothing of its characterization and role in trans-activating potential.

As a starting point for the present invention, Giguere et al., supra, demonstrated loss of activity in the glucocorticoid receptor based upon an assay measuring transcription activity, when random site-directed mutagenesis was performed at several locations of the molecule. As a followup, Hollenberg et al. deleted regions within the molecule, again demonstrating overall loss of transcription activity induced by such removal of stretches of amino acids.

It is an object of the present invention to identify and characterize the domain(s) responsible for trans-activation transcription activity, and the characterization of such domain(s) in respect of amino acid composition and sequence, to explore the functional interaction of the domain(s), if any, with both the DNA-binding and ligand-binding domains of a given receptor, and finally, to exploit such knowledge via the manipulation of such identified and characterized transactivation transcription domain(s) so as to increase the overall transcription activity of the given receptor so manipulated.

The present invention thus provides novel hormone or hormone-like receptors that have been modified by advantage of knowledge of the identity and characterization of the trans-activation transcription activity domain(s), by modifications thereof so as to produce novel, heterologous receptors that have increased activity compared with the parent molecule. It is an object of the present invention to provide novel, heterologous, optionally hybrid receptors having increased trans-activation transcription activity and otherwise having DNA-binding and ligand-binding domains that may be borrowed from various different receptors. It is a further object of the present invention to provide novel assays whereby putative receptor agonists and antagonists can be screened and evaluated for potential commercial exploitation. See also Ptashne, *Nature* 335, 683 (1988).

SUMMARY OF THE INVENTION

The present invention is predicated upon the identification, isolation and characterization of the trans-activation transcription domains of intracellular hormone or hormone-like receptor polypeptides that has in turn enabled the discriminate characterization of the receptor itself, both in terms of physical attributes and the biological function and effect of their various domains. This information has in turn enabled the production of harnessed, recombinant systems useful for preparing the novel receptors hereof having augmented transcription activation properties.

It has been determined, based upon the information provided herein, that receptors contain trans-activation transcription domains that are position independent and autonomous in function. Thus, the present invention provides for novel hormone or hormone-like receptors wherein the trans-activation transcription domains are augmented in their ability to activate transcription. Such novel receptors of this invention contain trans-activation transcription domains additional to the parent molecule, positioned in a manner to provide further increase in transcription activity. These novel receptors may be hybrids wherein the DNA-binding and the ligand-binding domains are provided from receptors of the same or different class and/or species.

The present invention is also directed to the use of such novel receptors for in vitro bio-assays for determining the functionality of a putative receptor or a putative hormone or hormone-like material. Bio-assays may take the form, for example, of challenging a novel receptor hereof with one or more of a battery of test materials that have putative hormone or hormone-like activity and that can potentially modulate the bio-function of said receptor and monitoring the effect of said material on said receptor in an in vitro setting.

The present invention is further directed to the preparation of such novel receptors hereof via recombinant DNA technology in all relevant aspects, including a DNA molecule that is a recombinant DNA molecule or a cDNA molecule consisting of a sequence encoding said receptor or a trans-activation transcription domain thereof, and to requisite expression vectors operatively harboring such DNA comprising expression control elements operative in the recombinant host selected for the expression, and to recombinant host cells transfected with such operative expression vectors.

The present invention is further directed to a method for inducing the expression of DNA encoding a reporter molecule or other desired heterologous polypeptide comprising inducing transcription of the DNA encoding said polypeptide by a complex formed by a novel receptor hereof and a corresponding ligand capable of binding to said receptor, in an in vitro setting wherein said receptor and said DNA encoding said polypeptide are produced via recombinant expression in a transfected cell host system.

The present invention thus embraces a hormone or hormone-like receptor as a polypeptide having increased trans-activation transcription activity of a promoter with which it is associated, by virtue of its intrinsic ability to bind to a DNA sequence response element of said promoter or by its ability to associate with other polypeptide(s) that bind to said DNA sequence response element, and having trans-activation transcription activity greater than that of its corresponding parent receptor.

The present invention is directed to recombinant DNA technology in all aspects relating to the use as the characterization of the trans-activation transcription domain of a hormone or hormone-like receptor for DNA isolates production, including cross-hybridizable DNA isolates, devising expression vectors therefor, transfected hosts producing therewith and methods comprising a method of use utilizing such information to devise cells or cell lines harboring genetic information sufficient for such cells or cell lines to produce such receptors such that they can be used as such or in expression systems or in assays for determining the activity of corresponding putative ligands.

DETAILED DESCRIPTION OF THE INVENTION

General Methods and Definitions

Figure 1:
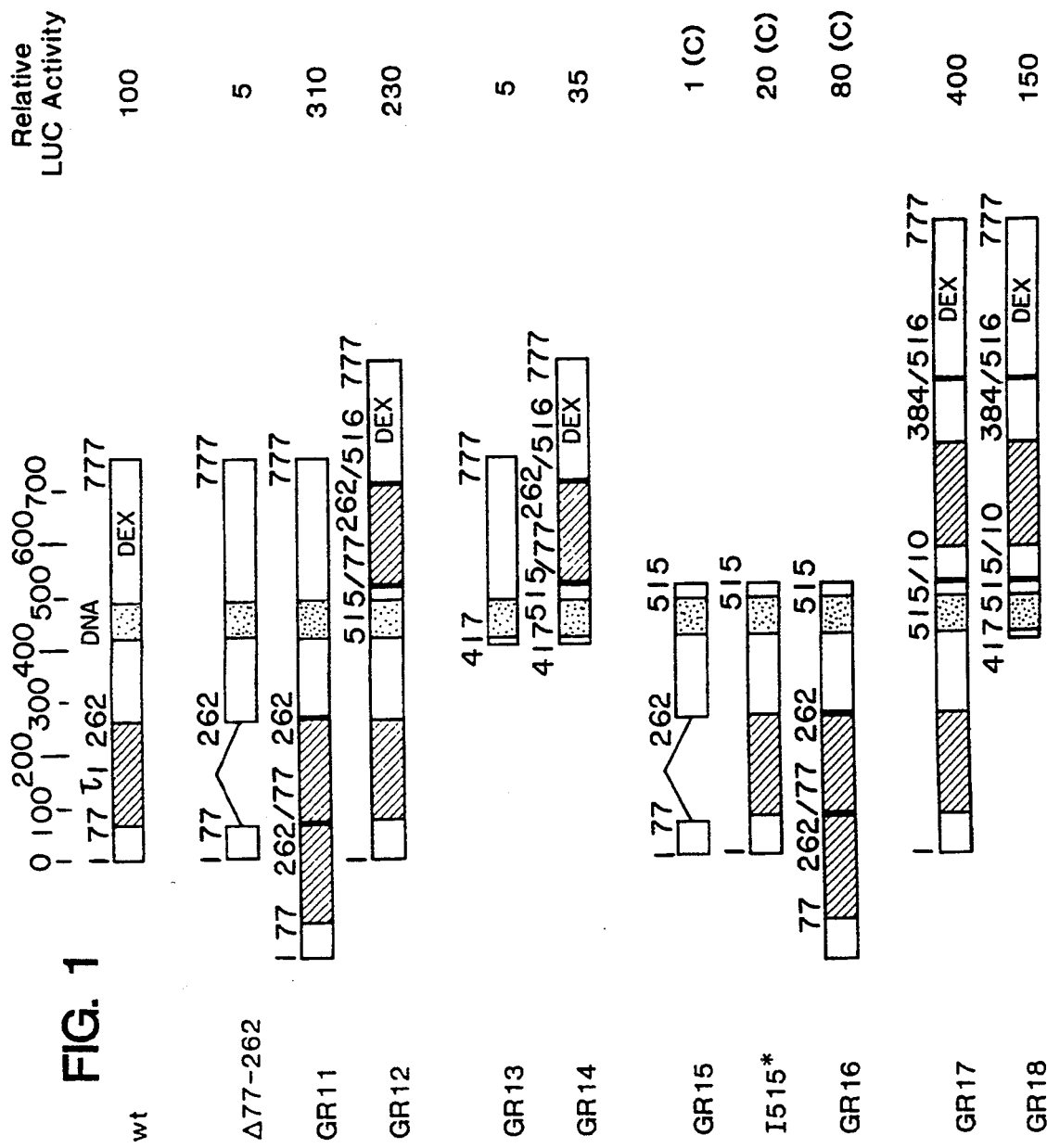
FIG. 1 depicts the identity, and transcription activity, of various human glucocorticoid receptors (hGR) entities hereof that have been modified from the parent molecule in the trans-activation transcription domains (tau$_1$). Wild-type hGR (wt) and tau1 mutants are schematically represented. Functional regions are hatched (tau$_1$), stippled (DNA-binding domain), or indicated by "DEX" (hormone binding domain). Numbers above each receptor define amino acid positions. Heavy vertical bars identify boundaries of an inserted fragment. Relative luciferase (reporter molecule) activity was measured by MTV-LUC using $10^{-7}$M dexamethasone (corresponding steroid), except receptors indicated by "C" after the activity which are constitutively active.

Amino acid identification uses the single- and three-letter alphabets of amino acids, i.e.:

| Asp | D | Aspartic acid | Ile | I | Isoleucine |
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

Steroid receptors hereof are prepared 1) having methionine as the first amino acid (present by virtue of the ATG start signal codon insertion in front of the structural gene) or 2) where the methionine is intra- or extracellularly cleaved, having its ordinarily first amino acid, or 3) together with either its signal polypeptide or conjugated protein other than its conventional signal polypeptide, the signal polypeptide or a conjugate being specifically cleavable in an intra- or extracellular environment. In all events, the thus produced receptor, in its various forms, is recovered and purified to a level suitable for intended use. See Supra.

The "hormone or hormone-like receptors" of this invention include the receptors specifically disclosed, for all species that cross-hybridization exists, most notably other mammalian receptors, as well as related (e.g., gene family) receptors of the same or cross-hybridizable species that are enabled by virtue of DNA isolation and characterization and use via cross-hybridization techniques from said specific receptors or from identification via immuno cross-reactivity to antibodies raised to determinants in the usual manner known per se. It also includes functional equivalents of all of the above, including interspecies or intraspecies receptors wherein DNA-binding and/or ligand-binding domains are swapped with one another, or otherwise differing in one or more amino acids from the corresponding parent, or in glycosylation and/or phosphorylation patterns, or in bounded conformational structure.

"Expression vector" includes vectors which are capable of expressing DNA sequences contained therein, where such sequences are operatively linked to other sequences capable of effecting their expression. It is implied, although not always explicitly stated, that these expression vectors may be replicable in the host organisms either as episomes or as an integral part of the chromosomal DNA. "Operative," or grammatical equivalents, means that the respective DNA sequences are operational, that is, work for their intended purposes. In sum, "expression vector" is given a functional definition, and any DNA sequence which is capable of effecting expression of a specified DNA sequence disposed therein is included in this term as it is applied to the specified sequence. In general, expression vectors of utility in recombinant DNA techniques are often in the form of "plasmids" which refer to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Apart from the novelty of the present invention involving the manipulation by means of repositioning or augmentation of the trans-activation transcription domains of a parent steroid receptor, it will be understood that the novel steroid receptors of the present invention may otherwise permissively differ from the parent steroid receptor in respect of a difference in one or more amino acids from the parent entity, insofar as such differences do not lead to a destruction in kind of the basic steroid receptor activity or bio-functionality.

"Recombinant host cells" refers to cells which have been transfected with vectors constructed using recombinant DNA techniques.

"Extrinsic support medium" includes those known or devised media that can support the cells in a growth phase or maintain them in a viable state such that they can perform their recombinantly harnessed function. See, for example, *ATCC Media Handbook*, Ed. Cote et al., American Type Culture Collection, Rockville, Md. (1984). A growth supporting medium for mammalian cells, for example, preferably contains a serum supplement such as fetal calf serum or other supplementing component commonly used to facilitate cell growth and division such as hydrolysates of animal meat or milk, tissue or organ extracts, macerated clots or their extracts, and so forth. Other suitable medium components include, for example, transferrin, insulin and various metals.

The vectors and methods disclosed herein are suitable for use in host cells over a wide range of prokaryotic and eukaryotic organisms.

In addition to the above discussion and the various references to existing literature teachings, reference is made to standard textbooks of molecular biology that contain definitions and methods and means for carrying out basic techniques encompassed by the present invention. See, for example, Maniatis, et al, *Molecular Cloning: A Laboratory Manual*, Cold Spring Harbor Laboratory, New York, 1982 and the various references cited therein, and in particular, Colowick et al.. *Methods in Enzymology* Vol 152, Academic Press, Inc. (1987). All of the herein cited publications are by this reference hereby expressly incorporated herein.

The foregoing description and following experimental details set forth the methodology employed initially by the present researchers in identifying and characterizing and preparing particular receptors. The art skilled will recognize that by supplying the present information including the location and makeup of the trans-activation transcriptional domain of a given receptor and how it can be manipulated to produce the novel receptors hereof, it is not necessary, or perhaps even scientifically advisable, to repeat these details in their endeavors to reproduce this work. Instead, they may choose to employ alternative, reliable and known methods, for example, they may synthesize the underlying DNA sequences encoding a particular novel receptor hereof for deployment within similar or other suitable, operative expression vectors and culture systems. Thus, in addition to supplying details actually employed, the present disclosure serves to enable reproduction of the specific receptors disclosed and others, and fragments thereof, using means within the skill of the art having benefit of the present disclosure. All of such means are included within the enablement and scope of the present invention.

DETAILED DESCRIPTION OF PARTICULARLY PREFERRED EMBODIMENTS

The present invention was premised upon use of the glucocorticoid receptor as a model herein for the preparation of novel modified entities thereof including hybrids of the glucocorticoid receptor with other receptors such as the thyroid receptor, particularly in the swapping of DNA-binding and ligand-binding domains to make up such hybrids. In each case the essence of this invention, namely, the repositioning and/or augmentation of the trans-activation transcription domain(s) so as to create novel receptors whose trans-activation transcriptional activity is increased over the parent, is illustrated herein using the glucocorticoid receptor as the parent or hybrids thereof upon which comparisons were made for the novel trans-activation transcription domain modified versions.

It will be understood therefore that for receptors that are known in the art, whether wild-type, hybrids, or functional equivalents as set forth herein, they are suitable as starting materials for the transactivation transcriptional domain(s) modifying aspects of the present invention.

EXAMPLES

The following examples detail materials and methods employed in the experimental procedures that follow:

Point Mutagenesis and Transcriptional Activation

To define systematically the role of the DNA binding domain in the function of the receptor, research employed extensive site-directed mutagenesis of this conserved region. By testing the role of individual amino acids this method has the potential to determine whether mutants which affect trans-activation are independent from those which influence DNA binding.

Figure 4:
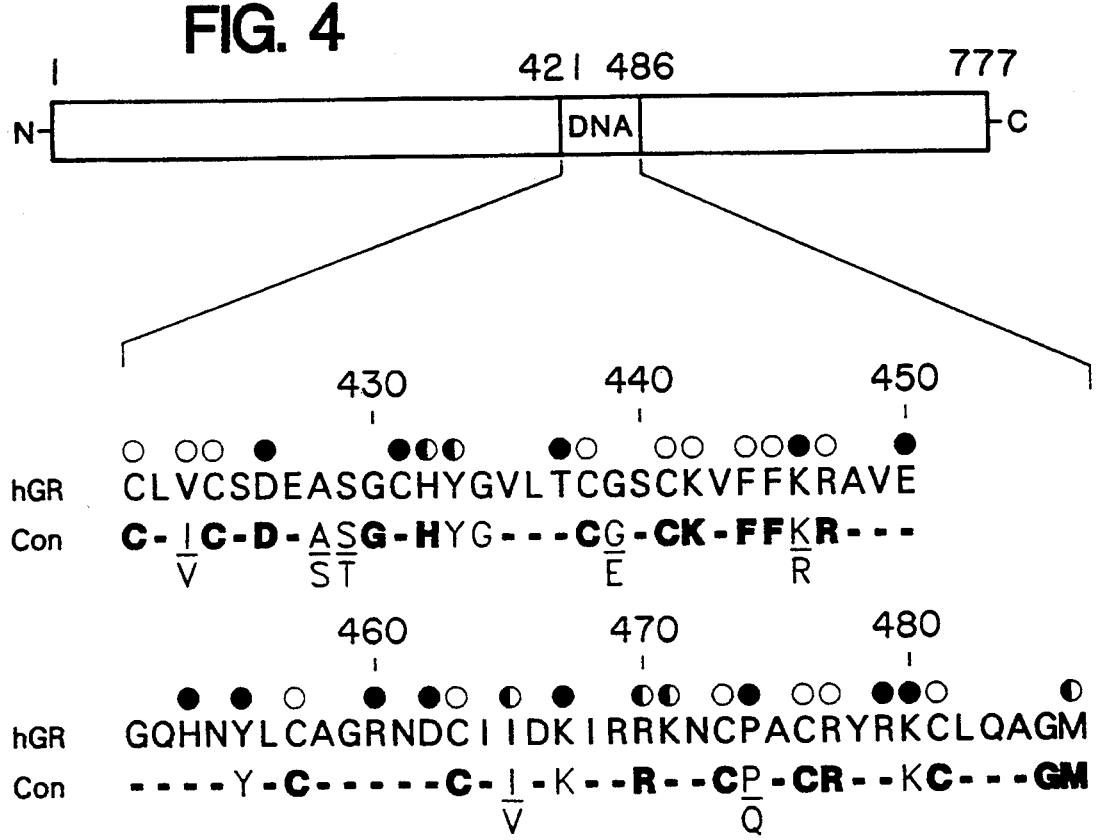
FIG. 4 sets forth the point mutational analysis of the hGR DNA-binding domain. The amino acid sequence of the hGR DNA-binding domain is given. Each line represents information believed to be encoded by part of a separate exon. The consensus sequence (con) for the steroid hormone receptor super-family is presented below the hGR sequence, with invariant (bold), conserved(standard type) and non-conserved (dashes) amino acids indicated. Amino acids converted to lysine are topped by circles. Transcription activity of mutants assayed with MTV-CAT and compared with hGR-SV are indicated as greater than 10% (filled circles), 1% to 10% (half-filled circles), and less than 1% (open circles).

The sequence of the hGR DNA binding region is given in FIG. 4, followed by the consensus sequence for the steroid hormone receptor superfamily. Among members of the superfamily, this domain contains 20 invariant and 12 conserved residues. All invariant amino acids, as well as eight conserved and eight non-conserved residues, were changed to glycine. The ability to stimulate transcription from the GR-responsive MTv promoter and to complex specifically with a glucocorticoid response element (GRE) DNA fragment in vitro was measured.

The steroid-dependent enhancement of transcription from MTV-CAT for each mutant is given in Table I and is indicated above each altered amino acid in FIG. 4. All activities are relative to the wild type receptor hGR-SB, which yields an average induction of approximately 1000 fold. Thus, even 1% residual activity is significant. The deletion mutants listed in Table I, delta420–451 and delta450–487, remove the first and second halves of the DNA binding domain, respectively, with the break point corresponding to an exon-exon boundary within the human mineralocorticoid and chicken progesterone receptor cDNAs. Both have no measurable activity indicating that neither "finger" alone is sufficient for activation.

Of the glycine point mutants, all of those which alter one of the nine invariant cysteine residues destroy activity, consistent with the idea that they are critical for function. An additional, non-conserved cysteine at position 431 is not necessary for function. Surprisingly, only five of the remaining 24 glycine mutants are completely inactive. The five non-functional alleles are all invariant residues, suggesting that they are involved in general aspects of DNA binding, not in determining sequence specificity. However, not all invariant residues are critical for function. For example, when aspartic acid 426 is converted to glycine there is almost no loss in activity. Seven out of eight mutants with conserved amino acids changed to glycine are functional, with half of this group retaining greater than 40% activity. Similarly, mutation of non-conserved amino acids within the DNA binding domain in no instance produces a receptor with less than 10% activity and generally causes little reduction in function. Thus, despite some significant exceptions, a good correlation exists between the conservation of an amino acid and the extent of functional loss when converted to glycine, with all invariant cysteines playing a critical role for function.

TABLE 1

Comparison of Transcriptional Activity and DNA Binding for hGR Glycine Mutants

| hGR Mutant | Relative CAT[a] Activity | Relative DNA Binding[b] in vitro |
| --- | --- | --- |
| hGR-SB | 100 | 100 |
| Δ420–451 | <1 | 1 |
| Δ450–487 | <1 | 1 |
| G421 | <1 | <1 |
| G423 | <1 | <1 |
| G424 | <1 | 1 |
| G426 | 75 | 75 |
| G431 | 80 | 10 |
| G432 | 10 | 30 |
| G433 | 2 | 1 |
| G437 | 20 | 8 |
| G438 | <1 | <1 |
| G441 | <1 | <1 |
| G442 | <1 | 60 |
| G444 | <1 | 1 |
| G445 | <1 | <1 |
| G446 | 40 | 6 |
| G447 | <1 | 2 |
| G450 | 60 | 50 |
| G453 | 90 | 60 |
| G455 | 80 | 6 |
| G457 | <1 | 2 |
| G460 | 55 | 90 |
| G462 | 80 | 40 |
| G463 | <1 | 1 |
| G465 | 1 | 1 |
| G467 | 40 | 6 |
| G470 | 3 | 4 |
| G471 | 10 | 6 |
| G473 | <1 | <1 |
| G474 | 60 | 95 |
| G476 | <1 | <1 |
| G477 | <1 | 1 |
| G479 | 65 | 40 |
| G480 | 90 | 50 |
| G481 | <1 | 3 |
| G486 | 10 | 1 |

[a] Activity was measured with MTV-CAT in CV-1 cells.
[b] The DNA binding assay is described elsewhere (Hollenberg et al., 1987). The value given was derived from total immunoprecipitated counts but reflects specific binding as determined by gel electrophoresis.

In vitro DNA Binding of Point Mutants

The CAT activity measured in the transcription assay is the sum of multiple individual functions including nuclear localization, DNA binding, dimerization and perhaps the allosteric events and protein-protein interactions that ultimately result in activation. If more than one essential function is encoded by the DNA binding domain, some of the non-functional point mutants may still retain their ability to bind DNA but fail to activate. To explore this possibility, each mutant protein was produced by transfection of the corresponding expression vector into COS-1 cells and assayed for its ability, in crude extracts, to form a specific DNA-protein complex with radiolabeled DNA. The activity of each mutant in this immunoprecipitation DNA binding assay is given in Table 1; the value shown represents specific binding of the GRE fragment. In general, there is good correspondence between the ability to activate transcription and to bind DNA in vitro. Mutants for which DNA binding activity is significantly lower than transcriptional activity, such as G446, G455, G467 and G486, may be unstable in vitro. The transcriptional activation measured for these mutants is a result of specific interaction with DNA in vivo, since deletion of GREs from the MTV promoter abolishes their activity.

Only a single mutant, G442, which converts the lysine directly following the first putative finger to glycine, has lost the capacity to efficiently stimulate transcription while maintaining affinity for DNA in vitro. The specificity of binding to GREs relative to non-specific sequences is only minimally affected, indicating that its dramatic loss in activity is not due to an inability to bind promoter sequences in vivo. This is an intriguing mutant because it suggests that DNA binding is not sufficient for activation. Perhaps G442 prevents a secondary event, such as an allosteric change, following the primary protein-DNA interaction. Despite this exception, these results demonstrate the cysteine-rich 66 amino acid region to embody the DNA binding domain. Indeed, although DNA binding is necessary for transactivation this function must be located in other regions of the receptor.

The G442 species has particular significance in terms of utility because it is the single species prepared that fails to result in activity but still shows evidence of substantial DNA binding. It is contemplated, for example, that an assay can be devised exploiting the property of both G442 and the I550* species. The I550* species lacks completely a ligand-binding domain, and as such, is not responsive to the presence or absence of hormone. The hormone to a specific ligand-binding site relieves the inhibition of the molecule to act as a trans-activation transcription factor. Lacking this domain means that the I550* species will always produce activity in an assay with or without presence of steroid. On the other hand, the G442 species in the same assay will always be inactive with or without steroid. By devising an appropriate assay where both receptors G442 and I550* are present in the system, initially there will be 100% activity based upon the contribution of the I550* species alone. As the appropriate steroid is added to the system, the activity observed will fall increasingly toward zero with time. Administration of a putative antagonist along with the appropriate steroid, if active as such, would restore the activity as the antagonist would interfere with the action of the steroid thus reducing the overall activity and a rebound in activity would be seen.

GAL4/hGR Chimeras

If DNA binding and $\tau$ functions are truly separable, the possibility exists to replace the hGR DNA binding domain with a non-receptor DNA binding domain to produce a hybrid activator protein with a new promoter specificity. To test this possibility, the hGR cysteine-rich region was substituted with the first 74 amino acids of yeast GAL4. These GAL4 amino acids are sufficient for sequence-specific DNA recognition, but have no transcriptional activation capability. The ability to trans-activate lies outside the DNA binding domain and is encoded in two separate regions of the protein. Therefore, in order to produce a functional transcription factor fusions between the GAL4 DNA binding domain and hGR must contain trans-activation functions contributed by the hGR To assay function of hGR-GAL4 hybrids, a GAL4-responsive promoter, deltaMTV-GAL-CAT, was constructed from MTv-OAT. This fusion gene was rendered GR-non-responsive and GAL4-inducible by replacement of GRE sequences with a synthetic GAL4 binding site. When measuring the activation of hGR and GAL4 on this promoter, hGR cannot produce measurable stimulation from this promoter, whereas GAL4 can increase CAT expression about 20-fold relative to a control expression vector. This is consistent with previous reports that GAL4 can function in higher eukaryotic cells. The stimulation by GAL4 is clearly mediated through the GAL4 synthetic binding site; deletion of this site renders the promoter non-responsive to GAL4.

Fusions between the GAL4 DNA binding domain and potential hGR activation domains Were examined for their ability to stimulate the GAL4-responsive reporter. To demonstrate that the hGR DNA binding domain is not required for the activity of this hybrid, the GAL4 DNA binding domain was substituted for the hGR DNA binding domain to produce the hybrid GgalG. (The hGR, including amino terminus (G-), DNA binding domain (G), and carboxy terminus (G), is referred to as G-G-G, respectively. Replacement of the hGR DNA binding domain with that of GAL4 generates G-gal-G.) The resultant hormone-dependent hybrid clearly can function in the absence of the hGR DNA binding domain and actually acts as a more potent transcription factor than GAL4 in this assay system, giving a 500 fold increase in CAT activity with addition of hormone. Unexpectedly, G-gal-G can also stimulate delta MTV-CAT without a GAL4 binding site, but only about 5% of that measured on delta MTV-GAL-CAT, The plasmid delta MTV-AT may contain a cryptic GAL4 recognition site that is revealed only with the stronger G-gal-G activator and not the weaker GAL4. Indeed, activation is dependent on the GAL4 DNA binding domain; G-gal-G is functional on deltaMTV-OAT whereas G-G-G is not, The trans-activation capability of G-gal-G must be determined by the amino- or carboxy-terminal regions of hGR, since the GAL4 DNA binding domain alone is inactive. Accordingly, each of these hGR regions was individually tested for its ability to complement the GAL4 DNA binding function. Both hybrids are functional with Ggal(delta) displaying constitutive activity while (delta)galG is fully hormone dependent. Therefore, autonomous trans-activation functions are embodied in both the N-terminal and C-terminal segments of the hGR, although subject to different constraints.

Rearranged and Partially Duplicated hGR Mutants

Figure 2:
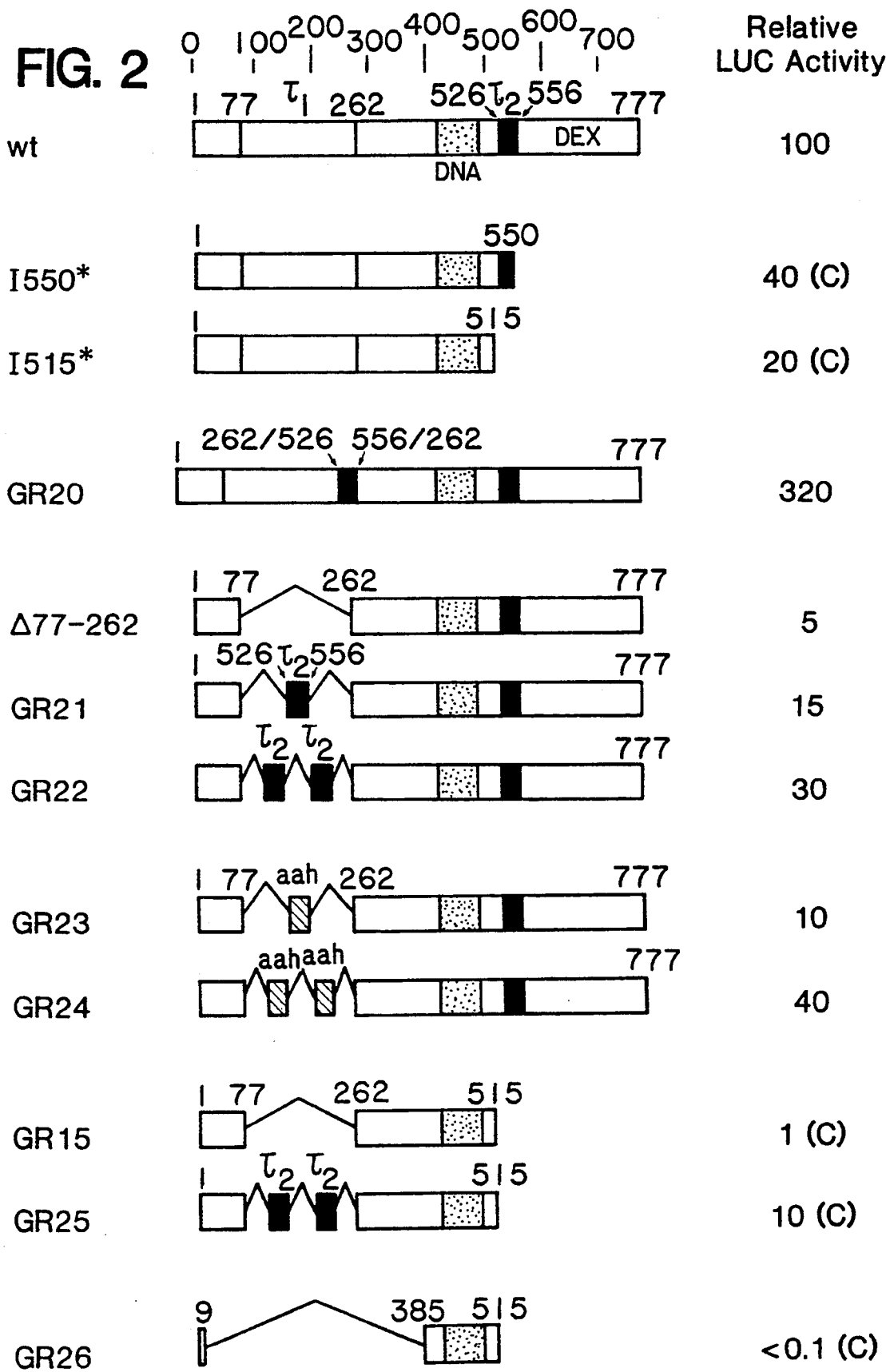
FIG. 2 sets forth the luciferase activity of various tau$_2$ receptors hereof. The wild-type hGR is represented at the top. The tau$_2$ region extends from amino acids 526 to 556 and is represented by a solid rectangle. Replacements of the tau$_1$ region are indicated by a solid rectangle (tau$_2$) or by hatched rectangles for the amphipathic alpha helix ("aah"). Relative luciferase activities were measured by MTV-LUC in the presence of $10^{-7}$ dexamethasone and are followed by "(C)" when hormone-independent. Asterisks indicate site of the amino acid end of truncated molecule.

Fusion with the GAL4 DNA binding domain demonstrated the presence of distinct trans-activation properties in the hGR amino-terminal 420 amino acids and carboxy-terminal 300 amino acids. Mutants of the hGR with $tau_1$ duplications were assayed on the luciferase derivative of MTV-CAT, MTV-LUC. Activity values determined with the MTv-luciferase fusion gene and MTV-CAT are equivalent for previously described deletion mutants. FIG. 1 shows the series of $\tau_1$ mutant derivatives and their luciferase activity relative to wild type receptor. Absence of $\tau_1$ reduces activity to 5%, while the tandem duplication mutant GRII acts as a "super" receptor with 310% activity. Mutants GR12, GR14, GR17 and GR18 reveal that $\tau_1$ can function between the DNA and hormone binding regions, as well as on the amino terminal side of the DNA binding domain, giving rise in each case to a hormone-dependent activator (FIG. 1). This indicates a remarkable flexibility of receptor structure. The ability of $\tau_1$ to increase activity is independent of both the amino and carboxy termini, as shown in FIG. 1 by comparison of GR13 and GR14 activities, and GR15 with I515* and GR16. The $\tau_1$ region may not account for all trans-activation ability in the amino terminus as shown by the 4-fold greater activity of GR18 relative to GR14, Also in support of this proposition, deletion of both $\tau_1$ and the carboxy terminus in GR15 leaves 1% residual activity, a ten-fold induction, which can be abolished by deletion of the majority of the amino terminus (compare GR15 and GR26, FIG. 2), A second region with potential trans-activation character is $\tau_2$, located at the very amino terminal end of the hormone binding domain (amino acids 526–556). This region has five negatively charged residues in a stretch of 18 amino acids and is implicated in receptor activity by the two-fold difference in activation of truncation $\tau_2$ mutants I550* and I515* (FIG. 2). To determine whether constitutes an activator domain it was introduced adjacent to, or in place of $\tau_1$. FIG. 2 shows that this region acts to give a 3-fold increase in activity when introduced into the amino terminus independent of $\tau_1$ (compare GR20 with "wt", GR21 with $\Delta77$–262). A second copy gives a further 2-fold increase, so that a pair of $\tau_2$ regions gives an overall increase in activity of six-fold (GR22). Therefore, like $\tau_1$, the position of $\tau_2$ in the receptor is flexible, its activity is cumulative and its function can be constitutive (e.g., GR25).

Figure 3:
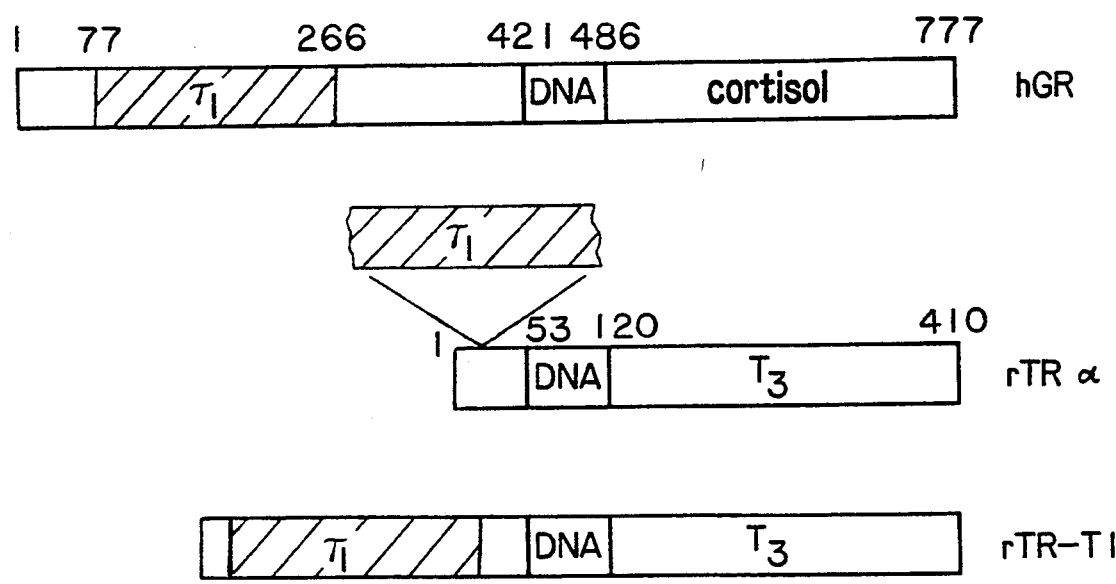
FIG. 3 depicts the construction of hybrid steroidal receptor of glucocorticoid-thyroid hormone receptors whose trans-activation transcription activity is increased by the addition of tau$_1$ domains. A segment of the human glucocorticoid receptor cDNA encoding amino acid 77 to 262 (encoding the tau$_1$ domain) was inserted in the rat alpha thyroid hormone receptor cDNA at a position corresponding to amino acid 21, in one or multiple copies. The parental receptor is rTR alpha with a BamHI linker inserted at the unique BstEII site in the amino terminus. Constructs were transfected into CV-1 cells with TRE-CAT and CAT activity measured in the absence or presence of T$_3$.

Constructions similar to the $\tau_2$ mutants GR21 and GR22 were constructed using the synthetic amphipathic α helix, "aah," containing 20% acidic residues and demonstrated to possess trans-activation properties in the context of yeast GAL4 (Giniger et al., Nature 330, 670(1987). The size and charge characteristics of the "aah" sequence are similar to the $\tau_2$ region, which led us to explore its potential activity in the context of the hGR. Indeed, a similar increase in activity of mutants with single or multiple copies of $\tau_2$ and aah is observed (FIG. 3; compare GR21 with GR23, GR22 with GR24), suggesting that these regions may perform equivalent functions. These results support and extend the notion of the modular nature of trans-activation domains.

Trans-activation (τ) Domains

We have defined discrete hGR trans-activation regions according to the following two criteria: deletion decreases activity and duplication increases it. By these standards two regions of the receptor, of 200 and 30 amino acids, encode trans-activation functions. The localization of these two regions does not exclude a role for additional activator sequences within the hGR. Examination of the primary sequences of $\tau_1$ and $\tau_2$ fails to reveal any obvious homology with the exception that both regions have acidic character. This property is noteworthy because activation domains in the yeast transcription factors GAL4 and GCN4, although lacking obvious sequence identity, are rich in acidic residues. This apparent similarity does not demonstrate that any of the identified activator regions in either GAL4, GCN4, or the glucocorticoid receptor are functioning through a common mechanism, although this seems likely. The potential for a common mechanism is further supported by the observation that the synthetic amphipathic α helix ("aah") sequence can functionally replace $\tau_2$ and to some extent $\tau_1$. The lack of obvious sequence and size relatedness of $\tau_1$, and $\tau_2$ and the yeast activation sequences leads to the view that trans-activation functions might be embodied by the net context of negatively-charged residues on the surface of the DNA-bound protein.

hGR Modularity

The modular nature of the hGR has emerged not only from primary sequence comparisons within the steroid receptor superfamily, but also by the ability to exchange functional domains to create novel chimeric activators. The DNA-binding domain of the hGR has been replaced with that of the human estrogen receptor (Green et al., Nature 325, 75 and Chambon, (1987) and with the unrelated DNA-binding domain from GAL4. Its position is not critical since it can function at the amino terminus. In addition, the DNA-binding domain can be placed amino or carboxy-terminal to both $\tau_1$ and $\tau_2$ without compromising function of these domains. Consistent with modular properties, the position of $\tau_1$ and $\tau_2$ is not critical and their multimerization leads to increased receptor function. Thus, we have been able to generate receptors with activity of up to four times that of the wild-type receptor or with altered DNA binding specificity. Hybrid receptors are still hormonally inducible indicating a non-specific mechanism whereby the hormone binding domain imposes a ligand-dependent effect on the rest of the molecule. Experimental detail and discussion follows:

Plasmid and point Mutant Construction

Plasmid hGR-SB was generated by recombination at the ClaI site between linker scanning mutants I532 and I403S (Giguere et al., Cell 46, 645 (1986)), I403S was derived from I403 by introduction of the SstI adaptor 5' GATCGAGCTCGC 3' into the BamHI site. This hGR derivative is parent to all Point mutants and is indistinguishable from wild-type receptor in DNA binding and transcriptonal activation. To convert the desired codon of hGR-SB to one encoding glycine, the SstI/BamHI, 400-nucleotide fragment from plasmid hGR-SB was first introduced into M13mp18 to yield single-stranded template. Synthetic oligonucleotides of 13–15 bases were then used to change the desired codon to GGN by standard techniques followed by re-introduction of the altered SstI/BamHI fragment into hGR-SB. Deletions Δ420–451 and Δ450–487- were generated with longer oligonucleotides (20mers); amino acid positions given define non-deleted residues at the deletion junction. Mutant sequences were directly determined from double-stranded plasmid DNA using alkaline denaturation (Hattori et al., Anal. Biochem 152, 232 (1986)) followed by chain termination of synthetic hGR primers.

Reporter plasmid MTV-CAT and its deletion derivative ΔMTV-CAT were generated as follows. The HindIII site of p8LcAT2 (Luckow et al., Nucl.Acids Res. 15, 5490 (1987)) was first destroyed to generate pTKCAT-H. The HSV-thymidine-kinase promoter of pTKCAT-H was then excised by digestion with 8amHI/BglII and replaced with the BamHI, MTV-LTR fragment of pMTV-TK (Kuhnel et al., J.Mol.Biol. 190. 367 (1986)), pLS-190/-181 or pLS-96/-88 (Buetti et al., J.Mol.Biol. 190, 379 (1986)) to generate MTV-CAT, −190/−181 MTV-CAT, or −96/−88 MTV-CAT, respectively, ΔMTV-CAT was constructed from −190/−181- and −90/−88 MTV-CAT by recombination between the HindIII sites of these mutants. ΔMTV-CAT was converted to MTV-GAL-CAT by introduction of the synthetic GAL4 binding site "17MX" (Webster et al., Cell 52, 169 (1988)) into the unique HindIII site. plasmid MTV-LUC was constructed by conversion of the HindIII site of pSVOA/L-A Δ5' (de Wet et al., Mol.Cell.Biol. 7, 725 (1987)) to XhoI and introduction of luciferase coding and SV40 polyadenylation sequences from this derivative (generated by BamHI digestion, Klenow polymerase I end-filling and XhoI digestion) into XhoI/SmaI-digested MTV-CAT.

G-gal-G was derived from pG525 (Laughon et al., Mol.Cell.Biol, 4, 260(1984)), primer-directed mutagenesis was used to introduce NotI and XhoI sites at coding-sequence nucleotides −10 to −3 and +223 to +228, respectively. The GAL4 DNA binding domain was excised from this derivative by digestion with NotI and inserted into pRShGR$_{NX}$ (Giguere et al., Nature 330, 624(1987)) in place of the endogenous DNA binding domain. GgalΔ and AgalΔ were produced by digestion of GgalG and AgalG, respectively, with XhoI, followed by end-filling and ligation. AgalG was constructed by introduction of a synthetic oligonucleotide duplex (ΔAN, 5' GTACCACCATGGGGC 3') containing a consensus ribosome binding site (Kozak, Nucl. .Acid.Res. 12, 857 (1984)), in place of the amino-terminal-coding, Asp718/NotI fragment of G-gal-G.

Generation of mutants Δ77-262, I515* and Δ9-385 has been described by Hollenberg et al., Cell 49, 39, (1987), τ₁ mutants were constructed using the BglII/BamHI fragment from I262 (Giguere et al., Cell 46, 645 (1986)), encoding amino acids 77-262 of the hGR. This fragment was inserted into the BamHI sites of hGR linker scanning mutants I262 and I515 to generate GR11 and GR12, respectively. GR13 was derived from pRShGR$_{NX}$ by replacement of the amino terminal coding sequences with the ΔAN adaptor described above. GR17 was created by insertion of the amino terminal coding BamHI fragment, generated by recombination between linker scanning mutants I9 and I384 (Giguere et al., supra,) into the BamHI site of I515. Mutant I550* was produced by recombination between the BamHI sites of mutants I550 and I696, thus shifting the reading frame after amino acid 550. This mutant was incorrectly described as δ532-697 in a previous report (Hollenberg et al., supra). To create τ₂ derivatives, an excisable τ₂ coding-fragment was generated by conversion of hGR nucleotides 1704-1709 and 1800-1805 (Hollenberg et al., Nature 318, 635 (1985)) to BamHI and BglII sites, respectively, using oligonucleotide-directed mutagenesis. The sequence encoding τ₂ was then introduced into the BamHI site of I262 to produce GR20 or in place of the BglII/BamHI fragment of I262 to generate GR21. GR23 was created by replacement of the BglII/BamHI fragment of I262 with a synthetic oligonucleotide duplex (5'GATCT GGAAT TACAA GAGCT GCAGG AACTA CAAGC ATTGT TACAA CAGCA AGAG 3') encoding the "aah" sequence (Giniger and Ptashne, 1987). Mutants with tandem copies of this sequence and τ₂ (GR24 and GR22) were generated by standard techniques (Rosenfeld and Kelly, 1986). Double mutant derivatives of constructions described above were generated by recombination at the ClaI site: GR14 from GR12 and GR13; GR15 from Δ77-262 and I515*; GR16 from GR11 and I515*; GR18 from GR13 and GR17; GR25 from GR22 and I515*; GR26 from Δ9-385 and I515*.

Immunoprecipitation DNA Binding

DNA binding was measured as described previously (Hollenberg et al., supra). Mutant receptor, obtained in a crude COS-1 cell extract after transfection, was incubated with a mixture of radiolabeled DNA fragments, one of which contained GREs. Receptor-DNA complexes were immunoprecipitated with receptor-specific antiserum and Staph A, freed of protein, counted Cerenkov, and then electrophoresed through a denaturing polyacrymide gel to verify specific binding. Total immunoprecipitated counts were compared. The presence of mutant hGR protein in each COS-1 cell extract was confirmed by Western blot analysis.

Transfection and Luciferase Assays

Transfection of CV-1 and COS-1 cells was as described previously (Giguere et al., and Hollenberg et al., supra) using 5 micrograms of each plasmid per 10 cm dish. Luciferase assays were performed as described (de Wet et al., supra).

Cell Culture and Transfection

Conditions for growth and transfection of CV-1 (African green monkey kidney) cells were as previously described (Giguere et al., Cell 46, 645 (1986)), except that the calcium phosphate precipitate was left on the cells for 4-8 hours, at which time the media was changed to DMEM with 5% T₃ free bovine serum minus or plus $10^{-7}$M T₃ (Sigma). Cells were harvested 36 hours after the addition of T₃, and CAT assays were performed as described (Gorman et al., Mol.Cell.Biol. 2, 1044 (1982); Hollenberg et al., Cell, 49, 39 (1987)). Typically, 5 μg reporter and 1 μg expression vector were cotransfected, along with 2.5 μg RSV-βgal as a control for transfection efficiency. Acetylated and non-acetylated forms of [¹⁴C]chloramphenicol were separated by thin layer chromatography, excised, and quantitated by liquid scintillation counting in Econofluor (DuPont) with 5% DMSO. β-galactosidase assays were performed as described (Herbomel et al., Cell 39, 653 (1984)). CAT activity is expressed as percent conversion divided by β-galactosidase activity.

Construction of Reporter and Expression Plasmids

Synthetic oligonucleotides corresponding to −169 to −200 of the rat growth hormone gene or a palindromic TRE (TCAGGTCATGACCTGA) (Glass et al., Cell 54, 313 (1988)) were inserted into a linker scanning mutant of MTV-CAT that has a Hind III site at position −190/−181 (Buetti et al, J.Mol.Biol. 190, 379 (1986)) or −190/−88 MTV-CAT, which has a HInd III site replacing the nucleotides between −88 and −190. Expression vectors were constructed for the thyroid hormone receptors by inserting the full-length cDNAs of pheA12 (Weinberger et al., Nature 324, 641 (1986)) and rbeA12 (Thompson et al., Science 237, 1610 (1987)) between the KpnI and BamHI sites of the pRS vector (Giguere et al., Cell 46, 645 (1986) and Nature 330. 124 (1987)).

Construction of Chimeric Receptors

The construction of hGR$_{NX}$ has been described (Giguere, Nature supra). To construct hTRβ$_{NX}$, the cDNA insert of phe A12 (Weinberger, Nature. supra) was subcloned between the KpnI and BamHI sites of M13mp19 and mutagenized by the method of Kunkel, pNAS 82, 488 (1985). The oligonucleotide used to create the NotI site changed three amino acids: Asp97 to Arg, Lys98 to Pro, Asp99 to Pro. The oligonucleotide used to create the XhoI site changed two amino acids: Thr171 to Leu, Asp172 to Gly. The mutant receptor cDNA was then transferred to the expression vector pRS (Giguere, Cell, Nature supra); hybrids were constructed by exchanging KpnI-NotI, KpnI-XhoI or NotI-XhoI restriction fragments between RShGR$_{NX}$ and RShTR$_{NX}$. RShGR$_{NX}$ has about 75% of wild-type activity, and RShTR$_{NX}$ has about 60% of wild-type activity. For the addition of τ₁ to rTRα, the unique BstEII site at amino acid 21 was changed to a BamHI site by inserting an oligonucleotide adaptor that encoded a BamHI site flanked by BstEII ends. This allowed the in frame insertion of a BamHI-BglII fragment encoding amino acids 77-262 of the hGR into this site. ΔTT and ΔGG were constructed by deleting the Asp718-NotI fragment of RShTR$_{NX}$ and RShGR$_{NX}$ respectively and replacing it with an oligonucleotide adaptor of a consensus ribosome binding site (Kozak Nucl.Acids Res, 12, 857 (1984)).

Amino acids 77 to 262 of the hGR, called τ₁, were inserted in frame after amino acid 21 of rTRα in one or multiple copies and the resulting hybrid receptors assayed for trans-activation. Table 2 shows that addition of one τ₁ domain increased activity by at least four-fold, while the presence of multiple such domains further increased activity. This is consistent with the modular nature of this domain, and demonstrates that the activity of thyroid hormone receptors can be augmented by the addition of a trans-activation domain from a different receptor.

TABLE 2

Activity of thyroid hormone receptor/$\tau_1$ hybrids.

| Receptor | # of $\tau_1$ domains | Relative CAT Activity[a] |
|---|---|---|
| RShGR | 1 | 0 |
| RSrTRα-Bm+ | 0 | 100 |
| RSrTR-T$^{1-1}$ | 1 | 1430 |
| RSrTR-T$_{1-2}$ | 2 | 1140 |
| RSrTR-T$_{1-3}$ | 3 | 1960 |
| RSrTR-T$_{1-4}$ | 4 | 820 |

[a]CAT activity is relative to the induced activity of RSrTR-Bm+, which is the rat alpha thyroid hormone receptor with the BstEII site at amino acid 21 changed to a BamHI site.

In certain experiments where the amount of receptor expression vector is increased from 1 μg to 5 μg, relative CAT activity was shown to increase several-fold.

The foregoing description details specific methods that can be employed to practice the present invention. Having detailed specific methods initially used to identify, isolate, characterize, prepare and use the receptors hereof, and a further disclosure as to specific entities, and sequences thereof, the art skilled will well enough know how to devise alternative reliable methods for arriving at the same information and for extending this information to other intraspecies and interspecies related receptors. Thus, however detailed the foregoing may appear in text, it should not be construed as limiting the overall scope hereof; rather, the ambit of the present invention is to be governed only by the lawful construction of the appended claims.

We claim:

1. A DNA molecule encoding a member of the steroid hormone superfamily of receptors having trans-activation transcription domains in addition to those of the parental receptor,
    wherein said additional trans-activation transcription domains are selected from the group consisting of $\tau_1$, $\tau_2$, and functional fragment(s) thereof,
    wherein said additional trans-activation transcription domains are independent of both the DNA-binding and ligand-binding domains of parent receptor, and
    wherein said additional trans-activation transcription domains are located outside of said DNA-binding and ligand-binding domains, if present.

2. An expression vector operatively harboring DNA encoding a receptor according to claim 1.

3. A recombinant host cell transferred with an expression vector according to claim 2.

4. A cell culture comprising cells according to claim 3 and an extrinsic support medium assuring the viability of said cells.

5. A process of preparing a human receptor which is a member of the steroid hormone superfamily of receptors having trans-activation transcription domains in addition to those of the parental receptor,
    wherein said additional trans-activation transcription domains are selected from the group consisting of $\tau_1$, $\tau_2$, and functional fragment(s) thereof,
    wherein said additional trans-activation transcription domains are independent of both the DNA-binding and ligand-binding domains of parent receptor, and
    wherein said additional trans-activation transcription domains are located outside of said DNA-binding and ligand-binding domains, if present,
    said process comprises expressing transfected DNA encoding said receptor in a host cell.

6. A process according to claim 5 further comprising recovering and purifying said receptor to enable its use in assays.

7. In a bioassay for determining the functionality of a hormone or hormone-like receptor, said bioassay comprising:
    (a) transfecting into receptor negative cells one or more expression vectors harboring an operative hormone responsive promoter/enhancer element functionally linked to an operative reporter or other desired DNA, and a construct containing an operative DNA sequence encoding said receptor,
    (b) culturing said transfected cells from step (a) in the presence or absence of extrinsic material having the putative ability to activate said hormone responsive promoter/enhancer element,
    (c) monitoring in said cells induction of the product of said reporter or desired DNA sequence, and
    (d) measuring in said cells the expression of reporter or other desired DNA, the improvement wherein said hormone or hormone-like receptor has increased trans-activation transcription activity compared with parent receptor, said increased activity due to additional transactivation transcription domains, relative to the parent receptor, wherein said domains are located said DNA-binding and ligand-binding domain of said receptor.

8. A DNA molecule encoding a member of the steroid hormone superfamily of receptors having trans-activation transcription activity, relative to trans-activation transcription activity of parental receptor,
    wherein said member of the steroid hormone superfamily of receptors contains a plurality of at least one parental receptor trans-activation transcription domain selected from the group consisting of $\tau_1$, $\tau_2$, and functional fragment(s) thereof, located outside of said receptor.

9. An expression vector operatively harboring DNA encoding a receptor according to claim 8.

10. A recombinant host cell transferred with an expression vector according to claim 9.

11. A cell culture comprising cells according to claim 10 and an extrinsic support medium assuring the viability of said cells.

12. A process of preparing a human receptor which is a member of the steroid hormone superfamily of receptors having increased trans-activation transcription activity, relative to trans-activation transcription activity of parental receptor,
    wherein said member of the steroid hormone superfamily of receptors contains a plurality of at least one parental receptor tarns-activation transcription domain selected from the group consisting of $\tau_1$, $\tau_2$, and functional fragment(s) thereof, located outside of said DNA-binding and ligand-binding domains of said receptor,
    said process comprises expressing transfected DNA encoding said receptor in a host cell.

13. A process according to claim 12 further comprising recovering and purifying said receptor to enable its use in assays.

* * * * *

UNITED STATES PATENT AND TRADEMARK OFFICE
CERTIFICATE OF CORRECTION

PATENT NO. : 5,310,662
DATED : May 10, 1994
INVENTOR(S) : Ronald M. Evans and Stanley M. Hollenberg It is certified that error appears in the above-indentified patent and that said Letters Patent is hereby corrected as shown below:

Column 17, line 52, change "transferred" to --transfected--.
Column 18, line 34, after "having" and before "transactivation", insert --increased--.
Column 18, line 42, after "outside" and before "of", insert --the DNA-binding and ligand-binding domain(s)--.
Column 18, line 45, change "transferred" to --transfected--.
Column 18, line 57, change "tarns" to --trans--.

Signed and Sealed this

Twenty-third Day of January, 1996

*Attest:*

BRUCE LEHMAN

*Attesting Officer*   *Commissioner of Patents and Trademarks*